United States Patent [19]

Turnbull et al.

[11] Plant 4,616

[45] Jan. 6, 1981

[54] PEAR TREE

[75] Inventors: Kenneth L. Turnbull, Depew, Okla.; Daniel K. Hybskmann, Shenandoah, Iowa

[73] Assignee: Henry Field Seed and Nursery Company, Shenandoah, Iowa

[21] Appl. No.: 31,985

[22] Filed: Apr. 20, 1979

[51] Int. Cl.[2] ..... A01H 5/00

[52] U.S. Cl. ..... Plt./36

[58] Field of Search ..... Plt./36

[56] References Cited

U.S. PATENT DOCUMENTS

| | | |
|---|---|---|
| P.P. 309 | 1/1939 | Ruedlinger . |
| P.P 380 | 4/1940 | Silvera . |
| P.P. 585 | 5/1943 | Shannon . |
| P.P. 728 | 3/1947 | Greiner . |
| P.P. 741 | 7/1947 | Moritz . |
| P.P. 757 | 9/1947 | Bowman . |
| P.P. 1,044 | 10/1951 | Cook . |
| P.P. 1,095 | 5/1952 | Kalle . |
| P.P. 1,153 | 12/1952 | Vistica . |
| P.P. 1,184 | 5/1953 | Eller . |
| P.P. 1,401 | 6/1955 | Dreyer . |
| P.P. 1,806 | 2/1959 | Dymond . |
| P.P. 1,992 | 12/1960 | Gebhard et al. . |
| P.P. 2,975 | 6/1970 | Anderson . |
| P.P. 3,193 | 5/1972 | Straw . |
| P.P. 3,291 | 1/1973 | Lowry . |
| P.P. 3,599 | 8/1974 | Griggs et al. . |
| P.P. 3,622 | 9/1974 | Anderson . |
| P.P. 3,705 | 4/1975 | Palacky . |
| P.P. 3,928 | 6/1976 | Johnson et al. . |
| P.P. 4,148 | 11/1977 | Cordy . |

*Primary Examiner*—Robert E. Bagwill
*Assistant Examiner*—James R. Feyrer
*Attorney, Agent, or Firm*—Lowe, Kokjer, Kircher, Wharton & Bowman

[57] ABSTRACT

A new variety of pear tree primarily distinguished by bearing extremely large fruit of globular-to-ovate form, weighing over two pounds in normal years and having a distinctive taste.

4 Drawing Figures

This discovery relates to a new and distinctive variety of pear tree.

The pear tree, a chance seedling of unknown parentage, was discovered in a cultivated area at a farm orchard in the county of Creek, Okla. in the vicinity of Depew, Okla.

The pear tree was asexually reproduced by T-budding on providence quince, cotonester acutifolia and pear seedling understocks, all with good success.

The accompanying color photographs illustrate this new variety of pear tree.

FIG. 3 is a close-up view of a characteristic pear from the tree.

FIG. 4 is a view of two pears in section, the right pear being in longitudinal section and the left pear being in lateral section.

Figure 1:
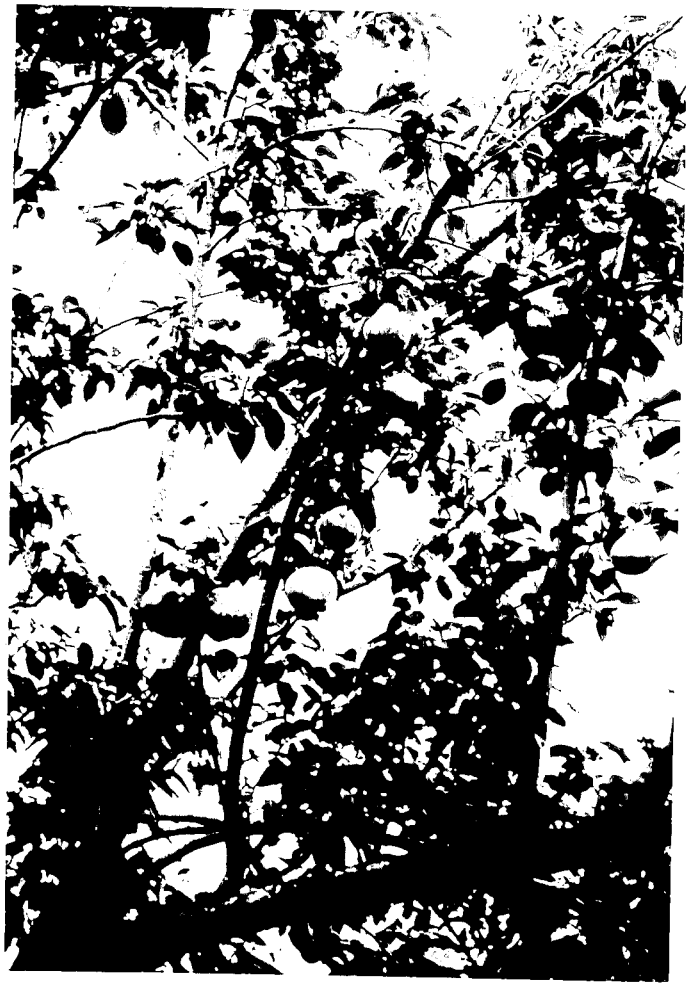
FIG. 1 is a view of a portion of the tree bearing fruit.
Figure 2:
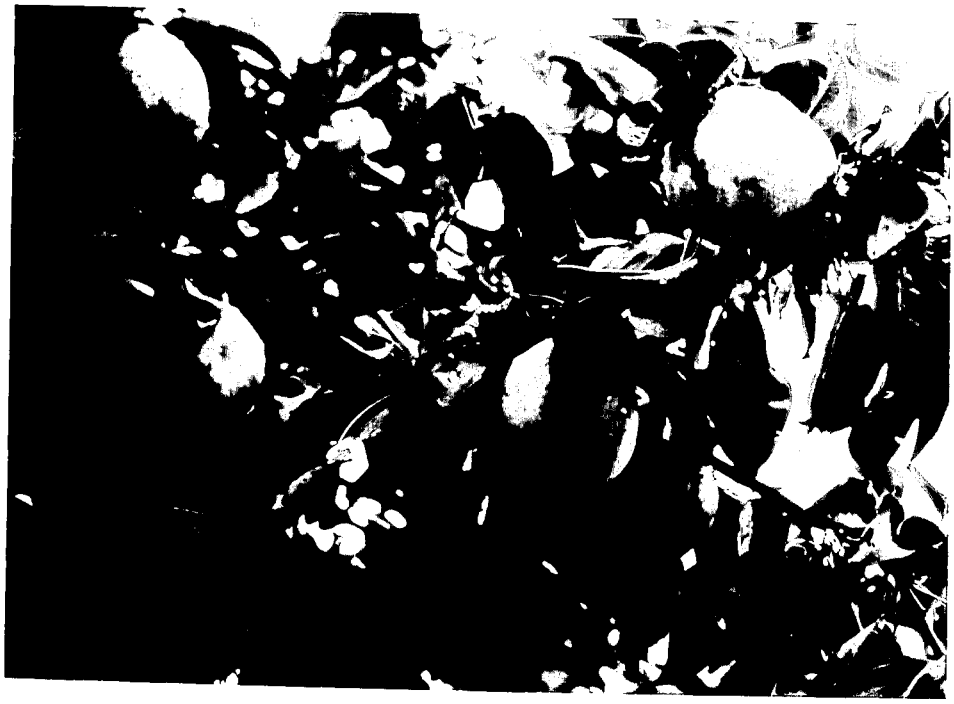
FIG. 2 is a close-up view of a portion of the tree bearing fruit.

This new and distinct variety of pear tree is chiefly characterized by its extremely large fruit. The shape is generally globular to ovate. In normal years, the typical fruit averages approximately 4½ inches long and 5 inches wide and weighs over 2 pounds. When present, the seeds are medium in size, but many of the fruits are seedless. The flesh is creamy white to ivory with a rather smooth consistency. Each fruit displays an interesting wavy basin similar to that of Delicious Apples. The taste of the fruit is distinctive and sprightly. At maturity, the fruit's flavor is somewhat reminiscent of a Yellow Delicious Apple.

The tree itself exhibits a strong, vigorous, upright spreading branching habit. Blooming extends over a long period of approximately one month and often, when the first blooms are damaged by freezing, the later flowers set fruits. Fire blight was observed on a Bartlett pear tree a few hundred feet from this new and distinct variety of pear tree but the disease has not been observed on this variety which indicates fire blight resistance.

The botanical details of this new and distinct variety of pear tree are as follows. Color definitions are referenced to Maerz and Paul Dictionary of Color (1950).

Tree:

*Size.*—Large.
*Height.*—24' tall at approx. 15 yrs. age.
*Vigor.*—Very vigorous.
*Growth.*—Upright, rapid, tall, spreading.
*Production.*—Very productive.
*Bearing.*—Early, regular bearer.
*Form.*—Upright, spreading, vase formed.
*Hardiness.*—Hardy.

Trunk:

*Size.*—Medium large.
*Diameter.*—12".
*Texture.*—Medium, shaggy.
*Color.*—Medium gray (8-C-7).

Branches:

*Old growth.*—Size — Large. Texture — Lightly shaggy. Color — Dark brown with gray overcast (7-C-7). Lenticels — Number — medium. Size — medium. Color — Medium gray (6-A-7).
*New growth.*—Size — Medium. Texture — Smooth. Color — Medium green with brown overcast (23-J-7). Lenticels — Number — Scattered. Size — Small. Color — Tan (6-A-8).

Roots: Pear seedling.

Leaves:

*Size.*—Leaves from current shoots — medium. Length — 2½–3". Width — 1½–1¾". Leaves from spurs — Large. Length — 3¼–3¾". Width — 1¾–2⅛".

*Form.*—Ovate, acuminate, upward fold from midrib.
*Thickness.*—Thick.
*Texture.*—Smooth, leathery.
*Margin.*—Serrulate.
*Petiole.*—Medium long. Length — 1¾". Thickness — 1/16" medium.
*Petiole color.*—Top side on new growth is dark pink (4-I-3).
*Color.*—Top side-dark semi-glossy green (23-J-11) underside-gray green (23-H-6).
*Venation.*—Pinnate.

Buds:
*Size.*—Small.
*Texture.*—Smooth, rather glossy.
*Color.*—Reddish brown (8-L-9).

Flowers:
*Blooming period.*—April 1–May 1, continues after Bartlett.
*Size.*—Medium.
*Color.*—White (17-B-1).
*Fertility.*—Self-fertile.

Fruit:
*Maturity when described.*—Soft ripe.
*Ripening period.*—Sept. 18–Oct. 18, 10 days later than Bartlett.
*Length of season.*—Long.
*Retention.*—Hangs well.
*Size.*—Very large, non-uniform — 4½" length, 5" width.
*Form.*—Globular to ovate.
*Stem.*—Short length — 1⅜", thickness—2/16"–3/16".
*Cavity.*—Shallow, acute, narrow, rough, russeted.
*Calyx.*—Large, open. Lobes — recurved, separated at base, calyx tube funnel shaped, stamens marginal.
*Basin.*—Deep, broad, abrupt, wavy.

Skin:
*Thickness.*—Medium.

*Texture.*—Brittle, rough, russeted, waxy.
*Color.*—Light yellow undercolor (19-L-2) with golden yellow overcolor (9-L-2) with slight pink blush (3-I-9) and reddish brown russet (6-A-12).
*Dots.*—Numerous, very small, rough, round, brownish tan (12-B-4).

Flesh:
*Color.*—Creamy white (10-B-1).
*Texture.*—Fine, crisp, melting, juicy.
*Flavor.*—Subacid, sprightly, cooling.
*Eating quality.*—Very good.
*Core.*—Median and small.
*Core lines.*—Meeting.
*Calyx tube.*—Length — long. Width — narrow. Form — funnel shaped.
*Seed.*—Sometimes seedless. Size — medium 4/16" wide, 5/16" long. Form — acute, plump. Color — brown (8-L-9).

Use: Market, dessert, culinary.
Keeping quality: Good.
Shipping quality: Good.
Resistance to:
*Disease.*—Shows resistance to fire blight.
*Cold.*—Good, blooms over long period.
*Wind.*—Heavy branches resist wind breakage but heavy fruiting can cause some breakage.
*Soil conditions.*—Sandy and clay soil plantings do well.
*Heat.*—Good.
*Drought.*—Very good.
Canning quality: Very good.
Ease of asexual reproduction: Easily reproduced by budding.

What is claimed is:

1. A new and distinct variety of pear tree, substantially as shown and described herein, distinguished by the physical characteristics of the fruit including its size, shape and taste.

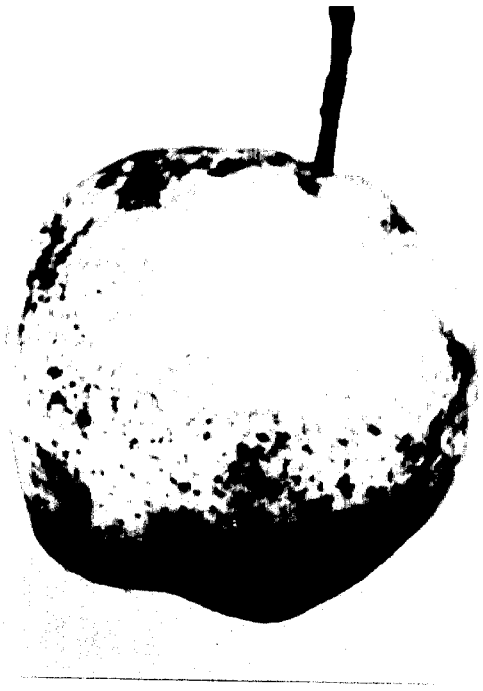
*Fig. 3.*
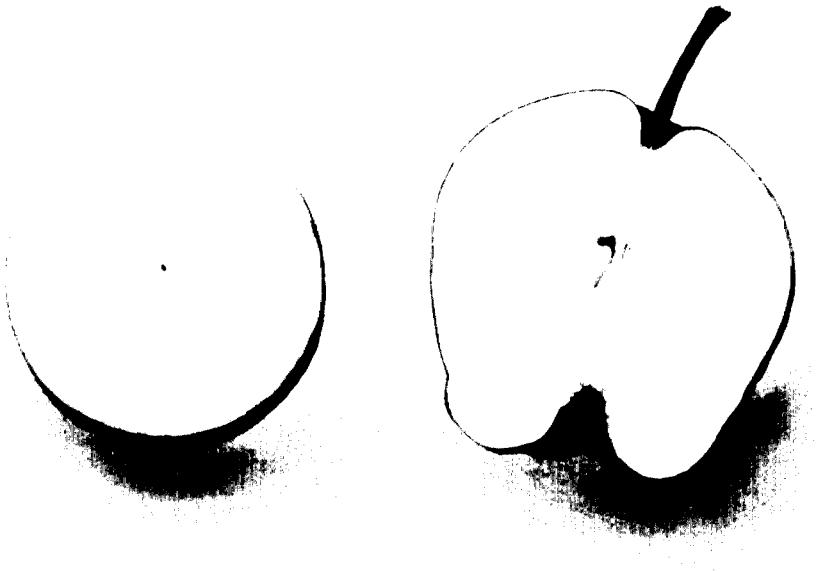

* * * * *